United States Patent [19]

Iyer

[11] Patent Number: 6,117,992

[45] Date of Patent: Sep. 12, 2000

[54] REAGENTS AND PROCESS FOR SYNTHESIS OF OLIGONUCLEOTIDES CONTAINING PHOSPHORODITHIOATE INTERNUCLEOSIDE LINKAGES

[75] Inventor: Radhakrishnan P. Iyer, Shrewsbury, Mass.

[73] Assignee: Hybridon, Inc., Milford, Mass.

[21] Appl. No.: 08/920,087

[22] Filed: Aug. 26, 1997

Related U.S. Application Data

[60] Provisional application No. 60/024,537, Aug. 26, 1996.

[51] Int. Cl.$^7$ .......................... C07H 19/10; C07H 19/20; C07H 1/02

[52] U.S. Cl. .................... 536/26.1; 536/25.3; 536/25.34

[58] Field of Search .............................. 536/25.3, 25.34, 536/26.1

[56] References Cited

PUBLICATIONS

Dahl et al. ACTA Chem. Scand. 43: 896–901, 1989.
Dahl et al. Tetrahedron Lett. 31: 3489–3492, 1990.
Bjergarde et al. Nucl. Acids Res. 19: 5843–5850, 1991.
Wiesler et al. J. Org. Chem. 61: 4272–4281, 1996.

*Primary Examiner*—Gary L. Kunz
*Attorney, Agent, or Firm*—Hale and Dorr LLP

[57] ABSTRACT

The invention provides new methods for synthesizing oligonucleotides containing at least one, and preferably all phosphorodithioate internucleoside linkages with less than 5% phosphoromonothioate contamination. This level of purity in the synthesis of phosphorodithoates has previously been very difficult to achieve with all existing methods. The invention further provides phosphorothioamidite nucleoside synthons comprising a sulfur protecting group that is stable under normal oligonucleotide synthesis conditions.

14 Claims, 4 Drawing Sheets

REAGENTS AND PROCESS FOR SYNTHESIS OF OLIGONUCLEOTIDES CONTAINING PHOSPHORODITHIOATE INTERNUCLEOSIDE LINKAGES

This application claims the benefit of U.S. Provisional No. 60/024,537 filed Aug. 26, 1996.

FIELD OF THE INVENTION

The invention relates to the chemical synthesis of oligonucleotides and to chemical entities useful in such synthesis.

BACKGROUND OF THE INVENTION

Oligonucleotides have become indispensable tools in modern molecular biology, being used in a wide variety of techniques, ranging from diagnostic probing methods to PCR to antisense inhibition of gene expression. This widespread use of oligonucleotides has led to an increasing demand for rapid, inexpensive and efficient methods for synthesizing oligonucleotides.

The synthesis of oligonucleotides for antisense and diagnostic applications can now be routinely accomplished. See e.g., *Methods in Molecular Biology*, vol. 20: *Protocols for Oligonucleotides and Analogs*, pp. 165–189 (S. Agrawal, Ed., Humana Press, 1993); *Oligonucleotides and Analogues: A Practical Approach*, pp. 87–108 (F. Eckstein, Ed., 1991); and Uhlmann and Peyman, supra. Agrawal and Iyer, *Curr. Op. in Biotech*, vol. 6:12, 1995; and *Antisense Research and Applications* (Crooke and Lebleu, Eds., CRC Press, Boca Raton, 1993). Early synthetic approaches included phosphodiester and phosphotriester chemistries. Khorana et al., *J. Molec. Biol.*, vol. 72:209, 1972, discloses phosphodiester chemistry for oligonucleotide synthesis. Reese, *Tetrahedron Lett.*, vol. 34:3143–3179 (1978), discloses phosphotriester chemistry for synthesis of oligonucleotides and polynucleotides. These early approaches have largely given way to the more efficient phosphoramidite and H-phosphonate approaches to synthesis. Beaucage and Caruthers, *Tetrahedron Lett*, vol. 22:1859–1862 (1981), discloses the use of deoxynucleoside phosphoramidites in polynucleotide synthesis. Agrawal and Zamecnik, U.S. Pat. No. 5,149,798 (1992), discloses optimized synthesis of oligonucleotides by the H-phosphonate approach.

Both of these modern approaches have been used to synthesize oligonucleotides having a variety of modified internucleotide linkages. Agrawal and Goodchild, *Tetrahedron Lett.*, vol. 28:3539–3542 (1987), teaches synthesis of oligonucleotide methylphosphonates using phosphoramidite chemistry. Connolly et al., *Biochemistry*, vol. 23:3443 (1984), discloses synthesis of oligonucleotide phosphorothioates using phosphoramidite chemistry. Jager et at., *Biochemistry*, vol. 27:72 (1988), discloses synthesis of oligonucleotide phosphoramidates using phosphoramidite chemistry. Agrawal et al., *Proc. Ant. Acad. Sci. USA*, vol. 85:7079–7083 (1988), discloses synthesis of oligonucleotide phosphoramidates and phosphorothioates using H-phosphonate chemistry.

Synthesis of certain types of modified oligonucleotides remains problematic, however. For example, synthesis of oligonucleotides containing phosphorodithioate internucleoside linkages has been plagued by oxidation of the phosphorodithioate internucleoside linkage to a phosphorothioate internucleoside linkage. Using a β-cyanothyl group to protect the sulfur moiety from oxidizing during the phosphorodithioate synthesis has been used in a previous approach with limited success and has resulted in high levels 8–9% of contaminanting phosphormonothioate incorporated into the phosphorodithioate product (Dahl et al, *Acta Chem. Scand.* 1989, 43, 896–901; Dahl et al, *Tetrahedron Lett.* 1990, 31, 3489–3492; Bjergarde et al, *Nucleic Acid Res.* 1991, 19, 5843–5850). Beaton et al, *Oligonucleotides and Analogues: A practical approach*; Eckstein, Ed.; IRL Press 1991;pp 109–135, discloses an improved procedure for synthesizing phosphorodithioate oligonucleotides. However, even in this procedure, at least 2–4% of the phosphorodithioate internucleoside linkages were oxidized to phosphorothioates and moreover, the synthons containing the 2,4-dichlorobenzyl group used to block the sulfur are highly unstable to oxidation and do not remain stable through the course of a single synthesis. Wiesler and Caruthers, *J. Org. Chem.*, 1996, 61, 4272–4281, disclose yet another improved procedure for phosphorodithioate synthesis, however this procedure is also plagued with 2–5% phosphoromonothioate contamination incorporated into the phosphorodithioate oligonucleotide product.

One attractive feature of the phosphorodithioate internucleoside linkage is that it is achiral. Thus, this internucleoside linkage can be used to make oligunucleotides which are stereochemically pure. In contrast, the phosphorothioate internucleoside linkage exists as $R_p$ and $S_p$ enantiomers. Thus, oligonucleotides containing phosphorothioate internucleoside linkages exist as racemic mixtures which contain $2^n$ sterichemically distinct species, wherein n represents the number of phosphorothioate internucleoside linkages present in the oligonucleotide. Accordingly, even low levels of oxidation of the phosphorodithioate internucleoside linkages to phosphorothioates can convert a stereochemically pure oligonucleotide preparation to a relatively complex racemic mixture.

There is, therefore, a need for improved reagents and processes for phosphorodithioate oligonucleotide synthesis. Ideally, such reagents and processes should be suitable for use in existing oligonucleotide synthesis protocols. There is further a need for oligonucleotides having exclusively phosphorodithioate internucleoside linkages as well as for oligonucleotides which contain phosphorothioate linkages.

SUMMARY OF THE INVENTION

The invention provides new methods for synthesizing oligonucleotides containing phosphorodithioate internucleoside linkages with less than 5%, and preferably less than 2% phosphoromonothioate contamination. This level of purity in the synthesis of phosphorodithoates has previously been very difficult to achieve with all existing methods. Thus, the invention also provides a population of phosphorodithioate-containing oligonucleotides with less than 5% and preferably less than 2% contaminating phosphoromonothioate incorporated therein. Additionally, the invention further provides nucleoside synthons for phosphorodithioate synthesis having a sulfur protecting group that is stable under normal oligonucleotide synthesis conditions.

One aspect of the invention provides novel synthons for phosphorodithioate synthesis comprising a sulfur protecting group (shown as "Y"), the monomer synthon having the general structure I:

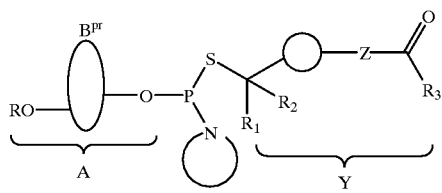

wherein ◯ is aryl, heterocyclic, heteroaryl, polyaromatic, cycloalkenyl, alkenyl, alkynyl; $R_3$ is aryl, heterocyclic heteroaryl, polyaromatic, alkenyl and substituted derivatives thereof, alkynyl or combinations of alkenyl moieties and alkynyl moieties; X is S, NH or O; $R_1$ and $R_2$ may be the same or different hydrocarbon moiety; R is a 5' OH blocking group (see e.g. Sonveaux in Methods in Molecular Biology Vol 26: Protocols for Oligonucleotide Conjugates pp 28–36 (S Agrawal, Ed., Humana Press, 1994), preferably dimethoxytrityl or trityl, B is a nucleoside base; $^{Pr}$ is a base protecting group, such as any suitable base labile group as is known in the art for the protection of exocyclic amino groups such as benzoyl groups or isobutyryl groups; A represents a nucleoside moiety which is a deoxyribonucleoside, a ribonucleoside, a substituted ribonucleoside wherein the 2' position of the ribose moiety is substituted with an O-lower alkyl group containing 1–6 saturated or unsaturated carbon atoms, or with an -O-aryl or O-allyl group having 2–6 carbon atoms wherein such alkyl, aryl or allyl group may be unsubstituted or may be substitued, e.g., with halo, hydroxy, trifluromethyl, cyano, nitro, acyl, acyloxy, alkoxy, carboxyl, carbalkoxyl or amino groups; and

represents a cyclic or acyclic amino functionality. The sulfur protecting group is represented as Y. Such monomer synthons are suitable for use in the well known phosphoramidite synthetic chemistries.

The configuration of structure 1 and the preferred embodiments thereof are particularly advantageous for effectively preventing oxidation of the sulfur during oligonucleotide phosphorodithioate synthesis, thereby preventing undesirable phosphoromonothioate contamination of the synthesis product. Thus, in another aspect, the invention provides a method for synthesizing oligonucleotides comprising phosphorodithioate internucleotide linkages at a higher purity level than has previously been achieved. This new method comprises sequentially coupling nucleoside monomer synthons of the invention having the sulfur protecting groups in accordance with the invention to produce a sulfur protected oligonucleotide, followed by a sulfurization step with any suitable sulfurizing reagent as is well known in the synthesis of oligonucleotides, and after the desired nucleotide length is reached, deprotection of the base protecting group and optionally, at the same time, deprotection of the sulfur protecting group with a chemoselective removing reagent. The method according to the invention preferably utilizes the well known phosphoramidite chemistries. In another embodiment of the invention the same protected phosphorodithioate moiety may be generated using H-phosphonate chemistry, and subsequently deprotected to the desired phosphorodithioate free of contaminating phosphoromonothioate.

The use of these novel reagents and methods of the invention provides many advantages. For example, phosphorodithioate containing oligonucleotides are synthesized with almost no phosphoromonothioate (chirally mixed) contamination resulting in the synthesis of oligonucleotides comprising internucleotide linkages which are achiral. Such achiral phosphorus internucleotide linkages have been found to be very advantageous when incorporated into antisense oligonucleotides for therapeutic use as they are highly stable toward both chemical and enzymatic hydrolysis. Moreover, studies have indicated that phosphorodithioate oligonucleotides have biophysical and biological properties which make them ideally suited for antisense applications, including but not limited to the activation of RNase H which is believed to be essential for antisense activity in vivo.

In addition, the reagents and methods of the invention may be used to produce a population of oligonucleotides comprising mixed chemical backbones such as a combination of one or more linkages of phosphorodithioate, methylphosphonate phosphorothioate or phosphodiester wherein the oligonucleotide population comprises less than 2% contaminating phosphoromonothioate incorporated therein. Oligonucleotides comprising such mixed backbones may be synthesized in order to maintain the overall advantages provided by the achiral nature of the phosphorodithioate linkage coupled with a stereocontrolled synthesis of the P-chiral phosphorothioate or P-chiral methylphosphonate linkages which make up the mixed backbone of the desired oligonucleotide.

DETAILED DESCRIPTION OF THE INVENTION

Figure 1:
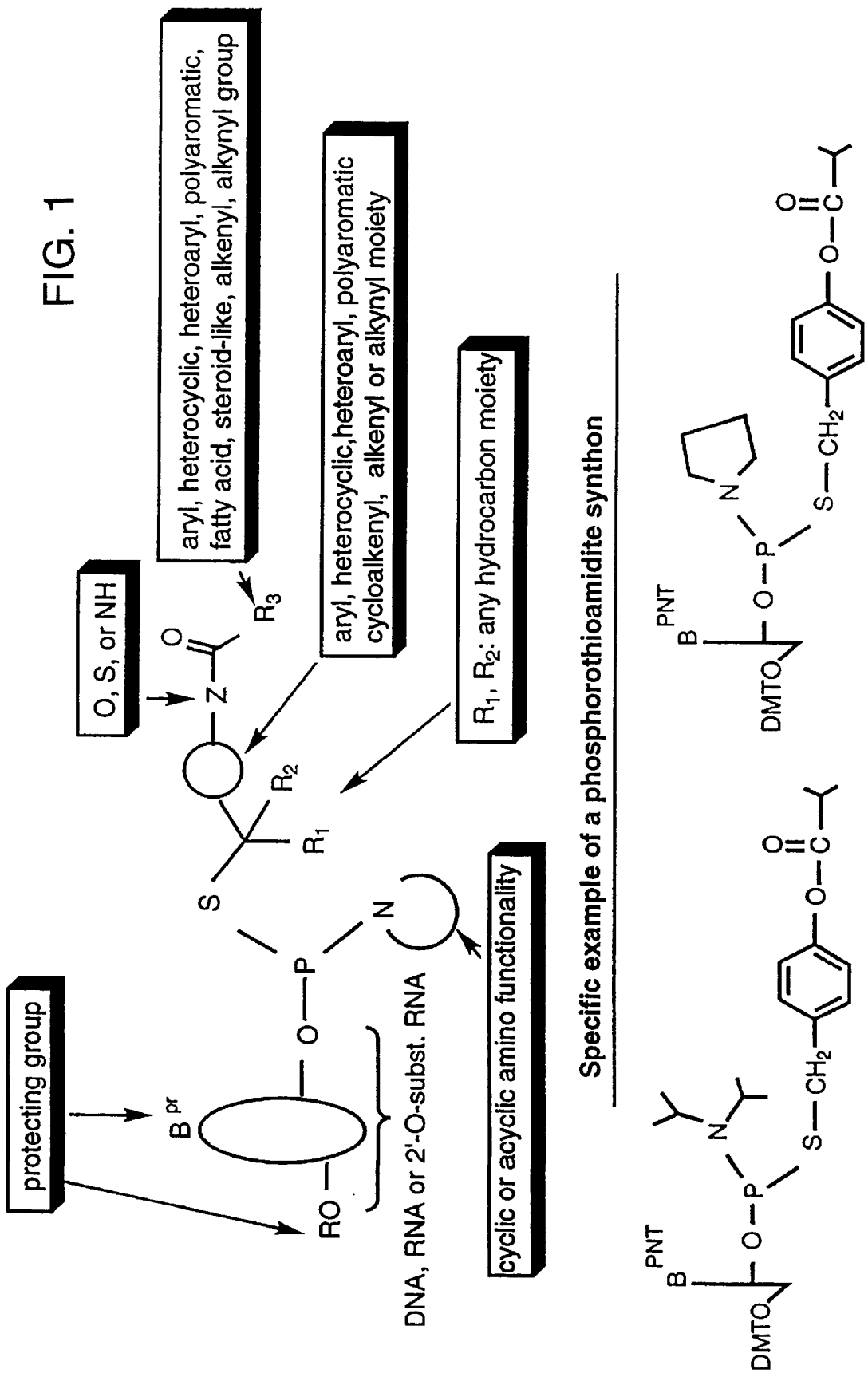
FIG. 1 is a schematic of the general structure of the phosphorothioamidite synthon of the invention with the sulfur protecting group as well as examples of the structures of specific phosphorothioamidite synthons in accordance with the invention.

The invention relates to the chemical synthesis of oligonucelotides containing phosphorodithioates and to chemical entities useful in such synthesis and the phosphorodithioate-containing oligonucleotide product of such synthesis. The patents and publications identified in this specification are within the knowledge of those skilled in this field and are hereby incorporated by reference in their entirety.

The invention provides new methods for synthesizing oligonucleotides containing at least one, and preferably all phosphorodithioate internucleoside linkages with less than 5%, and preferably less than 2%, and preferably less than 1% and most preferably undetectable amounts of phosphoromonothioate contamination. This level of purity in the synthesis of phosphorodithoates has previously been very difficult to achieve with all existing methods. The invention further provides phosphorothioamidite nucleoside synthons comprising a sulfur protecting group that is stable under normal oligonucleotide synthesis conditions.

For the purposes of the invention, the term "oligonucleotide" includes polymers of two or more deoxyribonucleotide, ribonucleotide or 2'-O-substituted ribonucleotide monomers, or any combination thereof. In certain embodiments oligonucleotides will preferably have from about 5–50 nucleotides, preferably about 10–45 nucleotides, preferably about 12–40 nucleotides, preferably about 15–35 nucleotides. In embodiments of oligonucleotides according to the invention that have fewer than all phosphorodithioate linkages, the other internucleoside linkages may be of any of the known internucleoside linkages, and are preferably also achiral linkages or chirally pure linkages. In certain preferred embodiments these internucleoside linkages may be P-chiral phosphorothioate, phosphodiester, or P-chiral methylphosphonate linkages. The term oligonucleotide also encompasses such polymers having chemically modified bases or sugars and/or having additional substituents including without limitation lipophilic groups, intercalating agents, diamines and adamantane. For purposes of the invention, the term 2'-O-substituted means substitution of the 2' position of the pentose moiety with an -O-lower alkyl group containing 1–6 saturated or unsaturated carbon atoms, or with an O-aryl or allyl group having 2–6 carbon atoms wherein such alkyl, aryl or allyl group may be unsubstitued or may be substitued, e.g., with halo, hydroxy, trifluoromethyl, cyano, nitro, acyl, acyloxy, alkoxy, carboxyl, cabalkoxyl, or amino groups.

The phosphorothioamidite synthons in accordance with the invention have the following general structure I:

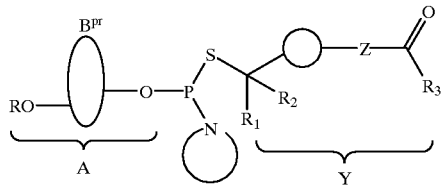

wherein ○ is aryl, heterocyclic, heteroaryl, polyaromatic, cycloalkenyl, alkenyl, alkynyl; $R_3$ is aryl, heterocyclic heteroaryl, polyaromatic, alkenyl and substituted derivatives thereof, alkynyl or combinations of alkenyl moieties and alkynyl moieties; X is S, NH or O; $R_1$ and $R_2$ may be the same or different hydrocarbon moiety; R is a 5'OH blocking group (see e.g. Sonveaux in Methods in Molecular Biology Vol 26: Protocols for Oligonucleotide Conjugates pp 28–36 (S Agrawal, Ed., Humana Press, 1994), preferably dimethoxytrityl or trityl, B is a nucleoside base; $^{pr}$ is a base protecting group, such as any suitable base labile group as is known in the art for the protection of exocyclic amino groups such as benzoyl groups or isobutyryl groups; A represents a nucleoside moiety which is a deoxyribonucleoside, a ribonucleoside, a substituted ribonucleoside wherein the 2' position of the ribose moiety is substituted with an O-lower alkyl group containing 1–6 saturated or unsaturated carbon atoms, or with an -O-aryl or O-allyl group having 2–6 carbon atoms wherein such alkyl, aryl or allyl group may be unsubstituted or may be substitued, e.g., with halo, hydroxy, trifluromethyl, cyano, nitro, acyl, acyloxy, alkoxy, carboxyl, carbalkoxyl or amino groups; and

represents a cyclic or acyclic amino functionality. The sulfur protecting group is shown in brackets as Y. Such monomer synthons are suitable for use in the well known phosphoramidite synthetic chemistries.

In one preferred embodiment of the invention, the phosphorothioamidite synthons in accordance with the invention have the following general structure II:

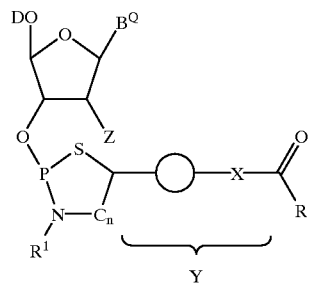

wherein ○ is aryl, heterocyclic, heteroaryl, polyaromatic, cycloalkenyl, alkenyl, alkynyl; R is aryl, heterocyclic heteroaryl, polyaromatic, alkenyl and substituted derivatives thereof, alkynyl or combinations of alkenyl moieties and alkynyl moieties; X is S, NH or O; n=1 or 0; $R^1$ is alkyl (1–15 carbons straight or branched), an aromatic or heterocyclic 5 or 6 membered ring comprising 1–5 heteroatoms, aralkyl or heteroaryl; B is a nucleoside base, D is a 5'OH blocking group (see e.g. Sonveaux in Methods in Molecular Biology vol 26: Protocols for Oligonucleotide Conjugates pp. 28–36 (S Agrawal, Ed., Humana Press, 1994), preferably dimethoxytrityl or trityl, Q is a base protecting group, such as any suitable base labile group as is known in the art for the protection of exocyclic amino groups such as benzoyl groups or isobutyryl groups; Z is H when the nucleoside is a deoxyribonucleoside is desired, Z is OH for a ribonucleoside, or Z is an O-lower alkyl group containing 1–6 saturated or unsaturated carbon atoms, or with an -O-aryl or O-allyl group having 2–6 carbon atoms wherein such alkyl, aryl or allyl group may be unsubstituted or may be substitued, e.g., with halo hydroxy, trifluromethyl, cyano, nitro, acyl, acyloxy, alkoxy, carboxyl, carbalkoxyl or amino groups (for a 2'O-substituted ribonucleotide). The sulfur protecting group is indicated by Y.

In a preferred embodiment of structure I or II, ○ is a phenyl group, a cis or trans ethenyl, or thiazole and R is isopropyl phenyl, cis or trans ethenyl, thiazole, pyrrole or furan. Specific, nonlimiting examples of suitable synthons of the invention are described in the examples and in the Figs.

In another preferred embodiment of structure I or II, Q is N-pent4-enoyl ($CH_2=CH(CH_2)_2CO$) (Iyer et al., J.Org. Chem, vol 60:8123–33 (1995). This base protecting group referred to herein as PNT, is particularly preferred (see FIG. 2 for structure). This group may also be used to protect the 2' hydroxy moiety of the ribose group as well as the 2'-O-substituted moiety of the ribose unit of the nucleotide during synthesis of phosphorodithioate RNA or 2'-O-substituted RNA. A chemoselective removing agent may optionally be chosen such that it can simultaneously remove the base and RNA protecting group and the sulfur protecting group of the protected dithioate intermediate to yield the phosphorodithoate during synthesis. In another embodiment, the N-pent-4-enoyl or other base protecting group, may preferably be removed without removing the sulfur protecting group using a chemoselective removing agent such as $Br_2$, $Cl_2$ and $I_2$ in pyridine/MeOH.

Figure 2:
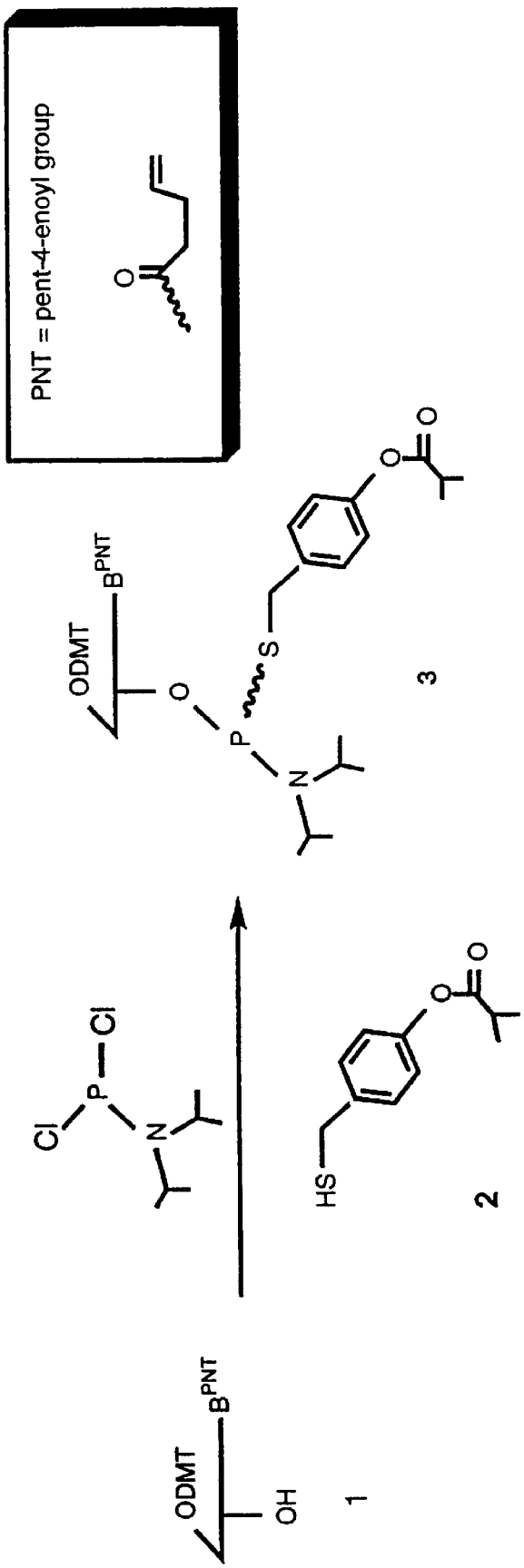
FIG. 2 shows the scheme for the synthesis of a phosphorothioamidite synthon of the invention as described in Example 1.
Figure 3:
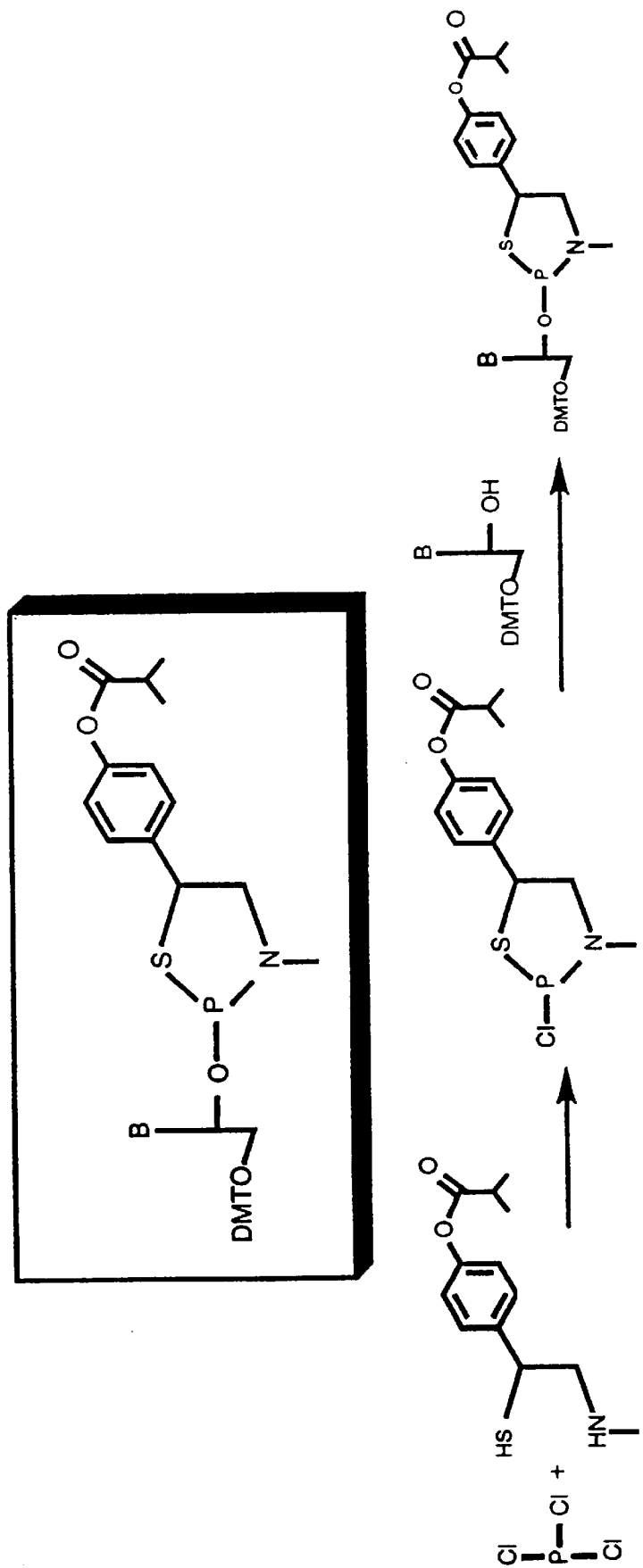
FIG. 3 shows the scheme for the synthesis of a thiaphospholidine synthon of the invention as described in Example 2.
Figure 4:
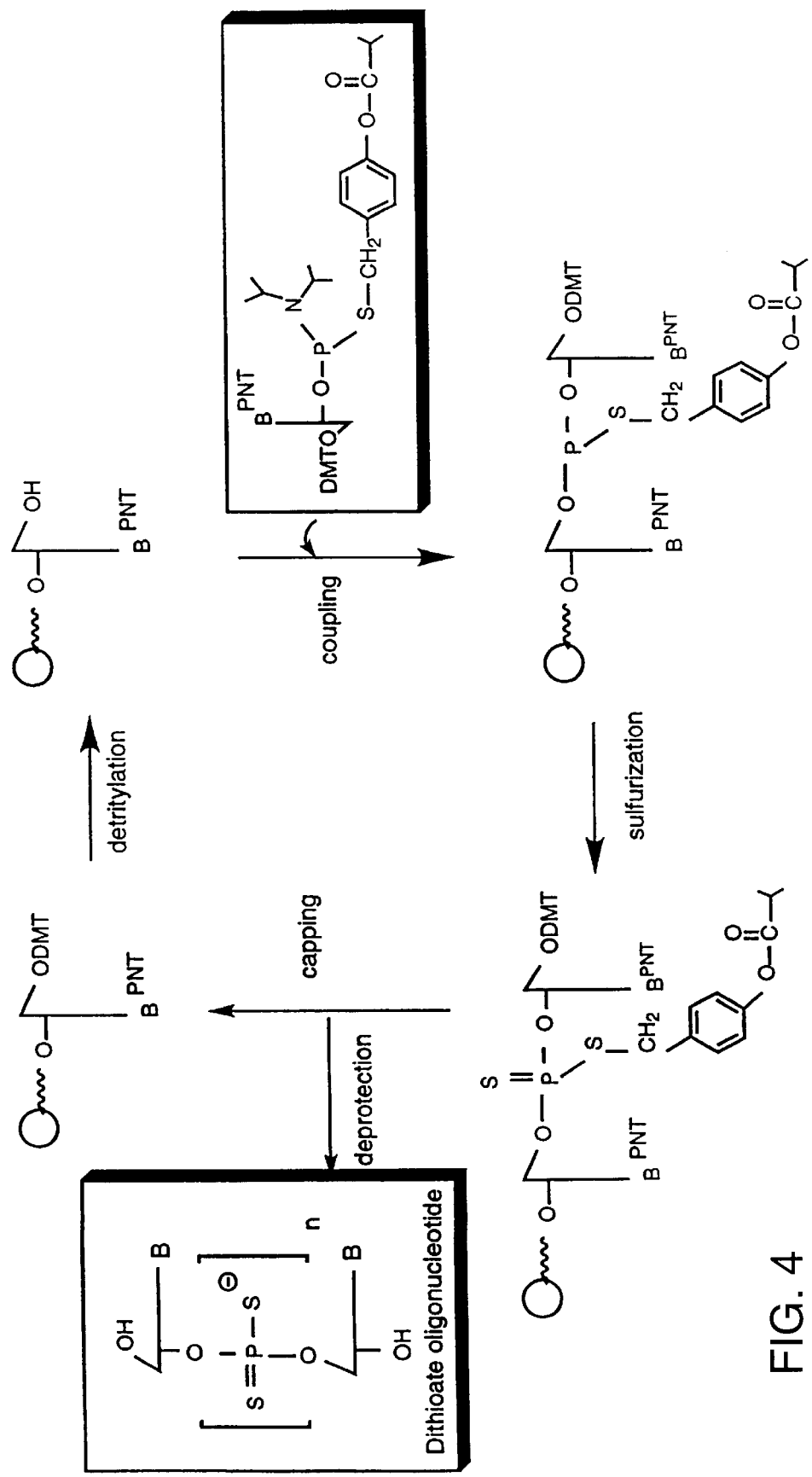
FIG. 4 shows the synthesis of dinucleoside phosphorodithoates using a phosphorothioamidite synthon of the invention as is described in Example 3.

Schemes for the synthesis of such monomers according to the invention are described in the Examples and shown in FIGS. 1 and 2.

The sulfur-protected synthons of the invention can be synthetically prepared with less than 5%, and preferably less than 2% contamination from the desulfurized (oxidized) phosphoramidite without subjecting the synthesis product to further purification procedures. The synthon also remains highly stable to oxidation post-synthesis. Therefore, in yet another aspect, the invention provides a population of phosphorothioamidite synthons of structure I comprising less than 2%, and preferably comprising less than 1% and most preferably comprising undetected levels of desulfurized phosphoramidite contamination.

In another aspect of the invention, the invention provides a simple, highly efficient process for synthesizing an oligonucleotide comprising from one to about all phosphorodithioate linkages using well known synthesis procedures and the novel chemical entities of the invention. In one embodiment, this process comprises condensing in the presence of 1H-tetrazole an phosphorothioamidite nucleoside comprising the sulfur protecting group of the invention, with another nucleoside, wherein at least one of the nucleosides has a nucleoside base-protective group, to produce adjacent nucleosides coupled by a phosphite linkage which is then sulfurized (e.g. elemental sulfur in pyridine/$CS_2$ or Beaucage reagent) to the protected phosphorodithioate, and eventually chemoselectively removing the sulfur protecting group preferably using a solution of $K_2CO_3$/MeOH.

Another embodiment comprises condensing in the presence of a suitable activator, such as pivaloyl chloride, a nucleoside H-thio-phosphonate with another nucleoside wherein at least one of the nucleosides has a base protecting group in accordance with an embodiment of the invention, to produce adjacent nucleosides coupled by a thio-H-phosphonate linkage, oxidizing the linkage in the presence of carbon tetrachloride with a protected thiol moiety in accordance with the invention (e.g. acyloxy-aryl mercaptan or heteroaryl mercaptan moiety as described above) to yield the protected dithioate, and removing, for example, acyloxy-aryl or heteroaryl sulfur protecting group of the invention as described above. Therefore another aspect of the invention is a method for synthesizing a phosphorodithioate oligonucleotide comprising the steps of: providing a thio-H-phosphonate nucleoside synthon; coupling in the presence of carbon tetrachloride, said synthon with a protected thiol moiety of the structure:

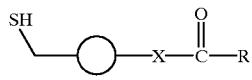

wherein ○ is aryl, heterocyclic, heteroaryl, polyaromatic, cycloalkenyl, alkenyl, alkynyl; R is aryl, heterocyclic heteroaryl, polyaromatic, alkenyl and substituted derivatives thereof, alkynyl or combinations of alkenyl moieties and alkynyl moieties; X is S, NH or O, to yield a sulphur protected thio-H-phosphonate intermediate and coupling said intermediate with a second thio-H-phosphonate synthon.

Synthesis may be carried out in solution phase or on a solid support as is known in the art. For solid support synthesis, after conventional detrytylation of a nucleoside linked to controlled pore glass (CPG) or any other suitable support such as polystyrene, a monomer synthon of the invention is coupled to the support linked monomer via conventional tetrazole activation for example. The resulting dinucleotide is oxidized with sulfur to the desired phosphorodithioate linkage. Unreacted CPG-bound nucleoside is then capped with acetic anhydride, for example, and the cycle is continued until the desired oligonucleotide length is achieved simultaneously. The sulfur protecting group of the invention and the base protecting groups are removed as described above and optionally the oligonucleotide can simultaneously be cleaved from the solid support.

Each of the above methods for the synthesis of phosphorodithioate oligonucleotides yields product with less than 5% and preferably less than 2%, preferably less than 1% and most preferably undetectable levels of contaminating phosphoromonothioate-containing product prior to any further post-synthesis procedures. Therefore, in yet another aspect, the invention provides a population of phosphoroidithioate-containing oligonucleotides comprising less than 5% and preferably less than 2%, and preferably comprising less than 1% and most preferably comprising undetected levels of contaminating phosphoromonothiate incorporated into the phosphorodithioate products.

In another preferred embodiment, oligonucleotides of mixed backbones may be prepared in accordance with the methods of the invention. Such oligonucleotides may comprise one or more phosphorodithioate linkages in combination with one or more phosphorothioate linkages, phosphodiester linkages or methylphosphonate linkages. If the phosphorothiate or methylphosphonate linkages are prepared in accordance with a stereocontrolled synthesis as is known in the art (see e.g. Iyer et al., *Tetrahedron Asymmetry*, 6: 1051–1054 (1995); and Stec et al., *Nucleic Acids Res*, vol. 19:5883–5888 (1991) ), an oligonucleotide comprising both achiral linkages and chirally pure linkages is expected to have the same advantages as an oligonucleotide comprising all achiral linkages. For example, as an antisense therapeutic, an oligonucleotide comprising both chirally pure methylphosphonate linkages and achiral phosphodithioate regions would maintain the consistent biochemical, biophysical and biological properties of a chirally pure methyl phosphonate but in addition with still activiate Rnase H via the phosphorodithioate linkages and maintain the beneficial stability toward both chemical and enzymatic hydrolysis which renders the achiral phosphorodithioate linkage so desirable.

Mixed backbone oligonucleotides according to the invention, comprise a population of oligonucleotides having at least one and preferably a region of phosphorodithioate nucleotide linkages wherein less than 5% and preferably less than 2%, preferably less than 1% and most preferably undetectable amounts of contaminating phosphoromonothioate is incorporated into the oligonucleotide population.

In some preferred embodiments of mixed backbone oligonucleotides according to the invention, several adjacent nucleosides comprising a first region of the oligonucleotide are connected by phosphorodithoate linkages and several other adjacent nucleosides comprising a second region are connected by a different type of oligonucleotide linkage such as another achiral linkage or a chirally pure linkage such as a P-chiral phosphorothioate or P-chiral methylphosphonate. These preferred oligonucleotides are referred to herein as "chimeric oligonucleotides" or "chimeras". In certain particularly preferred chimeric oligonucleotides according to the invention, the oligonucleotides comprises a phosphorodithioate region, and a P-chiral methylphosphonate region. In this context, a "phosphorodithioate region" is a region within an oligonucleotide of from about 2 to about 15 contiguous nucleosides linked to each other through phosphorodithioate linkages. A "P-chiral methylphosphonate region" is a region within an oligonucleotide of from about 4 to about 20 contiguous nucleosides linked to each other through P-chiral methylphosphonate linkages. A phosphodiester region is a region within an oligonucleotide comprising from about 2 to about 15 contiguous nucleosides linked to each other through phosphodiester linkages. In a preferred chimeric oligonucleotide of the invention, the oligonucleotide comprises a phosphorodithioate region flanked on either side by a methyl phosphonate region, or alternatively, a methyl phosphonate region flanked on either side by a phosphorodithioate region. In another preferred embodiment, a phosphodiester region is flanked on each side by a phosphorodithioate region or alternatively, a phosphorodithioate region is flanked on each side by a phosphodiester region.

Oligonucleotides according to the invention are useful for a variety of purposes. For example, they can be labeled with a reporter group and used as probes in conventional nucleic acid hybridization assays. They can also be used as antisense "probes" of a specific gene in an experimental cell culture or animal system and to evaluate the effect of blocking such specific gene expression. This can be accomplished by administering to a cell or an animal an oligonucleotide according to the invention that has a nucleotide sequence that is complementary to a specific gene that is expressed in the cell or animal to inhibit the expression of the specific gene, and observing the effect of inhibiting the expression of the specific gene. In this manner, oligonucleotides in accordance with the invention are preferable to traditional "gene knockout" approaches because they are easier to use and can be used to block gene specific gene expression at selected stages of development for differentiation.

Additionally, oligonucleotides according to the invention are useful in an antisense therapeutic approach. Therapeutic use of oligonucleotides according to the invention is for treating a disease caused by aberrant gene expression. This is accomplished by administering to an individual having the disease a therapeutically effective amount of an oligonucleotide of the invention, wherein, the oligonucleotide is complementary to a gene that is aberrantly expressed, wherein such aberrant expression causes the disease. Preferably, such administration should be parenteral, oral, sublingual, transdermal, topical, intranasal or intrarectal. It may be desirable to administer simultaneously or sequentially effective amount of one or more oligonucleotides of the invention as a single treatment episode.

As antisense therapeutics, the achiral, or partially achiral nature of the phosphorodithioate-containing oligonucleotides of the invention have the advantages described above including stability toward enzymatic and chemical hydrolysis as well as other biochemical and biophysical properties desirable for in vivo antisense use including activation of RNase H.

The following examples are intended to further illustrate certain preferred embodiments of the invention and are not limiting in nature.

EXAMPLE 1

Synthesis of Ester Phosphoramidites

To 5'-O4,4'-Dimethoxytrityl thymidine nucleoside (0.452 g, 0.830 mmol) in 5 mL of dry methylene chloride and 1 mL thiethylamine was added, followed by N,N-diisopropylphossphoramidic dichloride (0.2 g, 1 mmol) and the contents stirred at 0° C. for 5 min. Then the ester alcohol 2 (0.16 g, 1 mmol) was added. The reaction mixture was stirred at room temperature for 30 min. The solvent was then evaporated and the product 3 (0.5 g) was isolated following chromatography in silica gel (hexane/$CH_2Cl_2$/EtOAc/N(Et)$_3$, 1/1/0.5/0.1).

EXAMPLE 2

Synthesis of Thiaphospholidine Synthons

To 25 g of racemic mixture of the aminothiol in tetrahydrofuran (500 mL) and triethyl amine (150 g) was added 13.8 g of $PCl_3$, at −78° C., over a period of 2 hours. After the addition was over, the reaction mixture was allowed to warm to room temperature over a period of 20 hours. The mixture was filtered under argon to give the crude chlorophosphite, and was found to be of adequate purity for further reaction with the DMT-T-nucleoside.

Approximately 5.4 g of 5'-O-dimethoxytrityl thymidine was dissolved in a mixture of anhydrous ether (30 mL) and anhydrous triethylamine (6 mL). The solution was gradually added to 3.1 g of the chlorophosphite at room temperature and the solution stirred for 6 hours. The reaction mixture was poured into 200 mL of ice-cold water. it was then extracted with ethyl acetate (3×200 mL). The organic layer was evaporated to dryness to give ca. 5 g of the title compound as a pale yellow solid. Flash chromatographic purification (ethylacetate/methylene chloride/N(Et)$_3$, 80/19/1) on a silica gel column gives the tile compound ca 3.8 g as pale yellow foam.

EXAMPLE 3

Synthesis of Dinucleoside Phosphorodithoates using a Phosphorthioamidite Synthon Having obtained the nucleoside phosphoramidite with the acyloxyaryl protecting group, the stage was set for its use in solid-phase coupling reaction. Thus contacting a solution of the midite in acetonitrile with a CPG-gound nucleoside (10 μmol) for a period of two minutes in the presence of tetrazole as an activator followed by oxidation with 3H-benzodithiole-3-one-1, 1 dioxide (2% in acetonitrile) resulted in the formation of the dinucleoside phosphorodithioate triester with a coupling efficiency greater than 97% (as evaluated by trityl yields) (Iyer et al., J. Am. Chem. Soc., vol. 112:1253–54 (1990), and Iyer et al., J. Org. Chem. vol. 55:4693–98 (1990). Following the synthesis, the CPG-bound product was heated with aqueous ammonium hydroxide at 55° C. for 3 hours. Examination of the product revealed that the product was >96% the desired phosphorodithioate with the remaining approximately 4% material being the unreacted T nucleoside. The presence of phosphoromonothiate was less then 2% under these conditions.

What is claimed is:

1. A nucleoside synthon comprising a sulfur protecting group, said nucleoside synthon having the general structure:

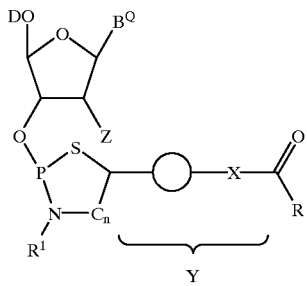

wherein ○ is aryl, heterocyclic, heteroaryl, polyaromatic, cycloalkenyl, alkenyl, alkynyl; R is aryl, heterocyclic heteroaryl, polyaromatic, alkenyl and substituted derivatives thereof, alkynyl or combinations of alkenyl moieties and alkynyl moieties; X is S, NH or O; n=1 or 0; $R^1$ is a straight or branched alkyl group having 1–15 carbon atoms, an aromatic or heterocyclic 5 or 6 membered ring comprising 1–5 heteroatoms, aralkyl or heteroaryl; B is a nucleoside base; D is a 5'OH blocking group; Q is a base-labile protecting group, capable of protecting exocyclic amino groups; Z is H, OH, an O-lower alkyl group containing 1–6 saturated or unsaturated carbon atoms, an -O-aryl or O-allyl group having 2–6 carbon atoms wherein the alkyl, aryl, or allyl group is unsubstituted or substituted with halo, hydroxy, trifluoromethyl, cyano, nitro, acyl, acyloxy, alkoxy carboxyl carbalkoxyl or amino; and Y is the sulfur protecting group.

2. The nucleoside synthon of claim 1 wherein ○ is a phenyl group, cis or trans ethenyl, or thiazole, and R is isopropyl phenyl, cis or trans ethenyl, thiazole, pyrrole or furan.

3. The nucleoside synthon of claim 1 wherein Q is the base protecting group, N-pent-4-enoyl.

4. The nucleoside synthon of claim 1 wherein D is dimethoxytrityl or trityl.

5. A method for synthesizing a phosphorodithioate oligonucleotide comprising the steps of coupling together two nucleoside synthons according to claim 1; sulfurizing the resulting intermediate to yield the protected phosphorodithioate oligonucleotide; and chemoselectively removing the sulfur-protecting ester moiety to yield the phosphorodithioate oligonucleotide.

6. A method for synthesizing a phosphorodithioate oligonucleotide comprising the steps of coupling a synthon of claim 1 to a nucleoside that is covalently bound to a suitable solid support; sulfurizing the resulting intermediate to yield the protected phosphorodithioate oligonucleotide; and chemoselectively removing the sulfur-protecting ester moiety to yield the phosphorodithioate oligonucleotide.

7. A method for synthesizing a phosphorodithioate oligonucleotide comprising the steps of: providing a thio-H-phosphonate nucleoside synthon; coupling in the presence of carbon tetrachloride, said synthon with a protected thiol moiety of the structure:

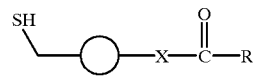

wherein ○ is aryl, heterocyclic, heteroaryl, polyaromatic, cycloalkenyl, alkenyl, alkynyl; R is aryl, heterocyclic heteroaryl, polyaromatic, alkenyl and substituted derivatives thereof, alkynyl or combinations of alkenyl moieties and alkynyl moieties; X is S, NH or O, to yield a sulphur protected thio-H-phosphonate intermediate and coupling said intermediate with a second thio-H-phosphonate synthon to yield the phosphorodithioate oligonucleotide.

8. A nucleoside synthon comprising a sulfur protecting group, said nucleoside synthon having the general structure:

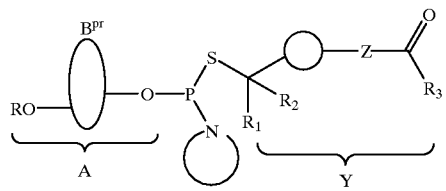

wherein ○ is aryl, heterocyclic, heteroaryl, polyaromatic, cycloalkenyl, alkenyl, or alkynyl; $R_3$ is aryl, heterocyclic heteroaryl, polyaromatic, alkenyl and substituted derivatives thereof, alkynyl or combinations of alkenyl moieties and alkynyl moieties; X is S, NH or O; $R_1$ and $R_2$ are the same or different hydrocarbon moiety; R is a 5'OH blocking group; B is a nucleoside base; $^{pr}$ is a base protecting group; A represents a nucleoside moiety which is a deoxyribonucleoside, a ribonucleoside, a substituted ribonucleoside wherein the 2' position of the ribose moiety is substituted with an O-lower alkyl group containing 1–6 saturated or unsaturated carbons atoms, or with an -O-aryl or O-allyl group having 2–6 carbon atoms wherein the alkyl, aryl or allyl group is unsubstituted or substituted; with halo, hydroxy, trifluoromethyl, cyano, nitro, acyl, acyloxy, alkoxy, carboxyl, carbalkoxyl or amino groups;

represents a cyclic or acyclic functionality; and Y represents the sulfur protecting group.

9. The nucleoside synthon of claim 8 wherein R is dimethoxytrityl or trityl.

10. The nucleoside synthon of claim 8 wherein $^{pr}$ is the base protecting group N-pent-4-enoyl.

11. The method of claim 5 wherein the two nucleoside synthons are coupled together in the presence of a catalyst.

12. The method of claim 11 wherein the catalyst is a tetrazole.

13. The method of claim 6 wherein the synthon is coupled to the nucleoside in the presence of a catalyst.

14. The method of claim 13 wherein the catalyst is a tetrazole.

* * * * *

UNITED STATES PATENT AND TRADEMARK OFFICE
CERTIFICATE OF CORRECTION

PATENT NO. : 6,117,992
DATED : September 12, 2000
INVENTOR(S) : Iyer

Page 1 of 1

It is certified that error appears in the above-identified patent and that said Letters Patent is hereby corrected as shown below:

Claims,

Claim 1,
Line 12, delete "O is" and insert -- Q is --
Line 19, delete "carboxyl" and insert -- carboxyl, --

Signed and Sealed this

Ninth Day of October, 2001

Attest:

NICHOLAS P. GODICI
Attesting Officer
Acting Director of the United States Patent and Trademark Office